United States Patent [19]

Reardon et al.

[11] Patent Number: 4,997,932
[45] Date of Patent: Mar. 5, 1991

[54] METHOD AND KIT FOR PURIFYING NUCLEIC ACIDS

[75] Inventors: Melissa A. Reardon; Lisa S. Klein, both of Indianapolis, Ind.

[73] Assignee: Boehringer Mannheim Corporation, Indianapolis, Ind.

[21] Appl. No.: 434,324

[22] Filed: Nov. 13, 1989

[51] Int. Cl.$^5$ .................. C07H 15/12; C12N 1/06; C12N 1/08; O07P 41/00

[52] U.S. Cl. ........................ 536/27; 536/28; 435/6; 435/259; 435/810; 435/267; 435/268; 435/269; 435/270; 435/280

[58] Field of Search ............ 536/27, 28; 435/6, 259, 435/267, 268, 269, 270, 280, 810

[56] References Cited

U.S. PATENT DOCUMENTS

| 4,482,482 | 11/1984 | Haff et al. | 536/28 |
| 4,800,159 | 1/1989 | Mullis et al. | 435/6 |
| 4,833,239 | 5/1989 | DeBonville et al. | 536/27 |

FOREIGN PATENT DOCUMENTS

| 0245945 | 11/1987 | European Pat. Off. | 536/27 |
| 0268946 | 6/1988 | European Pat. Off. | 536/27 |
| 0270017 | 6/1988 | European Pat. Off. | 536/27 |

Primary Examiner—Robert A. Wax
Assistant Examiner—Stephanie W. Zitomer
Attorney, Agent, or Firm—Felfe & Lynch

[57] ABSTRACT

The invention teaches a method and kit for purifying nucleic acid, such as DNA, from a sample, such as lysed cell or tissue sample. A sample is applied to an anionic exchange matrix column uniformly distributing the sample therein. The column bed is then washed with a weak ionic salt solution which is then removed. The anionic exchange material is optionally primed with an amount strong ionic salt solution which is insufficient to elute the nucleic acid from the column. The priming solution is then removed. An elution buffer is added either directly after the washing step or after the priming step. This is also a strong ionic salt solution of an ionic salt. The elution buffer removes the purified nucleic acid from the material. The method permits purification of nucleic acids without using organic solvents, and, if the priming step is used, in more concentrated form. Uniform distribution of the sample via disturbance of the matrix or column facilitates the purification.

27 Claims, 1 Drawing Sheet 1 2 3 4 5 6 7 8 9 10 11 12 13

DNA →

RNA →

1 2 3 4 5 6 7 8 9 10 11

DNA →

RNA →

METHOD AND KIT FOR PURIFYING NUCLEIC ACIDS

FIELD OF THE INVENTION

This invention relates to a method for purifying nucleic acids, such as DNA and RNA and mixtures thereof from a sample, as well as kits useful in performing such purification.

BACKGROUND AND PRIOR ART

Nucleic acids, i.e., DNA and RNA, are well known as the so-called "genetic blueprint" of all cell types. Be they prokaryotes or eukaryotes, cells require DNA and RNA for the production of various proteins needed for viability.

Much of the current work being performed in the biological sciences requires manipulation of pure nucleic acids. Transformation, transfection, Northern and Southern blots, polymerase chain reactions, and so forth, all require a ready source of purified nucleic acid material. In addition, purified nucleic acids are used in applications such as "DNA fingerprinting" in forensic sciences, so-called "RFLP" analysis, and other applications where purified DNA or RNA is necessary.

Nucleic acids do not exist in free form in cells; rather they interact with various molecules and organelles in vivo forming, e.g., nucleo-protein complexes. Biological materials present nucleic acid material that is encapsulated in protein coats or in association with membranes. See, in this regard Rodriquez and Tait, *Recombinant DNA Techniques, An Introduction* (Benjamin Cummings, 1983), pg. 37-38.

Standard methods for isolation of DNA call for lysis of the sample (tissue or cell), by various methods, in connection with various enzymes such as proteinase K. These procedures yield a mix of DNA and macromolecules which must be separated. One classic method for DNA purification utilizes an extraction reagent containing organic solvents, such as phenol and chloroform, optionally with isoamyl alcohol. See, in this regard Murmur, J. Mol. Biol. 3: 208-218 (1961); Gross-Bellard, et al., Eur. J. Biochem. 36: 32-38 (1973); Blin, et al., Nucl. Acid. Res. 3: 2303-2308 (1976). In these methods, the nucleic acids are separated into the aqueous phase of a two phase organic/non-organic (i.e., water) system. The aqueous layer having a lower density than the organic portion of the reagent, rises to the top of a mixture, from which it can be removed or extracted.

While this methodology is a standard one, it requires expensive reagents and equipment to perform, and a good deal of time. Additionally, phenol and chloroform are both noxious to use, cause burns on contact to skin and mucus membranes, require cumbersome safety apparatus, such as hoods to prevent inhalation and have been implicated as potential carcinogens. In addition, contamination of the aqueous, DNA containing layer by the organic solvent (phenol) is a ubiquitous problem. This contamination renders the DNA useless for further manipulations without additional purification procedures. Awareness of this problem leads to a need for the investigator to exercise extreme caution, especially with respect to the interface between the organic and non-organic layers. This can, and frequently does, lead to decreased yields of nucleic acids, and additional processing steps, such as "back-extraction" (i.e., the extraction of the remaining, mostly organic material, with additional aqueous solvents).

The patent literature describes the use of techniques such as those described supra in connection with other biochemical inventions. For example, U.S. Pat. No. 4,623,627 teaches obtaining double stranded DNA using the phenol/chloroform methodology described supra.

Another method used to separate DNA is cesium chloride gradient ultracentrifugation. See, Glisin, et al., Biochemistry 13: 2633-2637 (1974). In this methodology, a DNA solution is mixed with a cesium chloride solution or a mixture of cesium chloride and ethidium bromide. The mixture is then centrifuged, resulting in a gradient of increasing salt concentrations. DNA molecules band at positions within the gradient corresponding to their buoyant density.

This methodology, however, requires the use of an ultracentrifuge as well as expensive chemicals, and a good deal of time. While of interest, it is not the optimum approach, as is evidenced by the number of papers teaching variations on this general technique. See, e.g., Meese, et al., Gene Anal. Tech. 4: 45-49 (1986), where guanidine HCl is used in combination with the cesium chloride gradient technique.

A second group of methodologies, which may be referred to collectively as "column purification", is of more pertinence to the subject invention. In column purification, the nucleic acid containing sample is applied to a solid phase matrix. For example, Shoyab, et al., Meth. Enzymol. 68: 199-206 (1979) describe purification of genomic DNA using hydroxyapatite column chromatography. U.S. Pat. No. 4,649,119 teaches that hydroxyapatite may be used as a support to recover plasmids from Corynebacterium bacteria.

An additional type of column purification is taught by Potter, et al., Cancer Lett. 26: 335-341 (1985). This method uses a matrix of diethylamino ethyl (DEAE) sepharose, referred to hereafter as a "DEAE matrix".

A DEAE matrix presents a positively charged ion (N+) covalently bound to the matrix, together with a mobile counterion (Cl−). These mobile counterions are available for exchange, under suitable conditions, with other negatively charged ions, such as proteins and nucleic acid molecules. DEAE matrices are quite common in column separation, as is taught by Maniatis, et al., *Molecular Cloning, A Laboratory Manual* (Cold Spring Harbor Laboratories), pp. 130 and 164.

The first step in ion exchange column separation is application of the sample to the column. Standard methodologies instruct the investigator to apply the sample without disturbing the matrix bed. This is followed by a washing step, generally using a low salt buffer. Potter, et al., supra, call for washing the sample containing column with a buffer of 10 mM Tris, 1 mM EDTA, and 0.1 M NaCl. Variations may be seen in, e.g., European Patent Application 270 017, to Molecular Biosystems, Inc., teaching washing with a salt strength of from 0.2 to 0.5 M.

The step as described in these references removes impurities that are present in the applied sample. The salt concentration is kept low (i.e., a weak ionic strength buffer is used) because the ions in the salt solution will complete with the DNA bound to the column.

Following the wash step in which impurities are eluted, DNA is collected from the column via, e.g., elution. Here, a higher concentration of salt is required, because the very effect avoided in the washing step is now desired. Hence, in Potter, supra, elution is at 1.0 M NaCl, while the European Patent Application referred to supra elutes at anywhere from 0.5 M to 1.0 M, depending upon the nature of the nucleic acid and the column used. The amount of elution buffer used is desirably kept as low as possible. In practice, however, this aim is in conflict with the need to use a larger amount of buffer so as to elute all or as much of the nucleic acids as possible.

Other references teach different elution reagent strengths. U.S. Pat. No. 4,389,396, to d'Hinterland, e.g., teaches gradient elution using from 0.0 to 0.5 M NaCl. U.S. Pat. No. 4,649,119 to Sinskey teaches elution using 1.0 M potassium phosphate. Indeed, the strongest elution solution currently observed in the art is 1.0 M.

The ion exchange purification methodologies elaborated upon supra all adhere to the teaching in the art that instructs one to apply the same to the matrix surface without disrupting the matrix surface.

It has now been found, surprisingly, that upon creating a uniformly mixed slurry upon application of the sample, the nucleic acids are uniformly mixed throughout the matrix, leading to effective interaction between the nucleic acid molecules and the ion exchange matrix. This, in turn leads to effective recovery of purified, high molecular weight nucleic acids.

It has also been found that by including an optional "priming step" in which a high strength ionic salt solution is applied to the ion exchange matrix before elution of the nucleic acid allows the nucleic acid to be recovered in a smaller volume of elution buffer. This, too, is a result not to be expected from the prior art.

SUMMARY OF THE INVENTION

The invention is a method for obtaining a sample of pure nucleic acid. The method involves applying a nucleic acid containing sample, such as lysed prokaryote or eukaryotic cells, eukaryotic tissue, etc., or a "crude" or "semi-purified" sample of nucleic acids to an anionic exchange support. The sample is applied to the column in a manner which ensures uniform distribution of the sample thereon. Following this, a weak ionic salt solution is added to the column. This acts to remove impurities therefrom. This wash solution is then removed via, e.g., elution. The column may be "primed" by addition of a defined volume of a strong ionic salt solution. The priming solution, when added in a defined volume, surprisingly does not elute the nucleic acid from the column, but instead permits recovery of the nucleic acids in a more concentrated form, because the elution buffer which is then applied may be added in a smaller volume than is usually required.

Either immediately after the washing step, or after the optional priming step, an elution buffer or solution is applied. This removes purified nucleic acid from the column or matrix. The nucleic acid is then collected.

In applying the wash, priming, and elution reagents, the column bed (i.e., the DEAE matrix) is not disturbed, in contrast to the uniform distribution of the nucleic acid sample throughout the column bed.

The invention as described herein is a method universally adaptable for purification of nucleic acids of any type including prokaryotic and eukaryotic DNA, such as genomic DNA, as well as total RNA. In addition to the advantages described supra, the methodology uses no organic solvents in a simple process. It is thus safer, more time efficient and straightforward then the methodologies currently used in the art.

DETAILED DESCRIPTION OF PREFERRED EMBODIMENTS

Figures 1, 2:
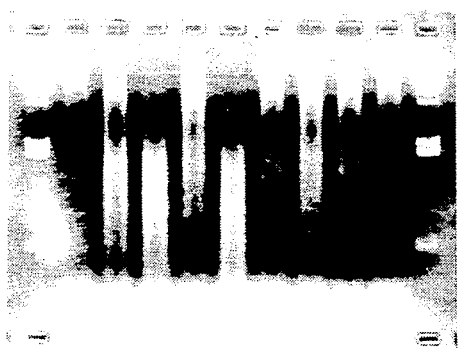
FIG. 1 shows the result of experiments extracting DNA from prokaryotes in accordance with the invention.
FIG. 2 shows separation of total nucleic acids from eukaryote tissue samples following the invention.

The invention as described herein is useful in the separation of nucleic acids from a sample, regardless of the source of the sample.

As is well known, when nucleic acids derive from prokaryotic and eukaryotic cells, lysis prior to the application of the sample to the column or support is required. The details of this preparation steps are set forth, infra, for various types of cells. Among the types of cells and tissues which can be used for purification of nucleic acids are all strains of *E. coli*, yeast, murine myeloma, and human buffy coat cells. Solid tissues are exemplified by rat hepatoma and homologous liver tissues. Mice tails, and other types of tissue may also be used.

The lysed sample is applied to an anion exchange support or column which has been equilibriated with a sample of low ionic strength solution, which is elaborated upon infra. The anion exchange support is a material which permits exchange of a mobile negative ion with negatively charged nucleic acids. Many anionic exchange materials are known to the art. Preferred are DEAE sepharose supports.

Following equilibration, the prepared sample is applied to the matrix, column or support, in a manner which permits uniform distribution of the sample throughout. This is accomplished via progressive disturbance of the matrix to form a uniform slurry of sample and matrix. By so doing, a uniform distribution of sample through the column bed is achieved. This can be performed via various methods available to the skilled artisan.

While the sample may be applied "neat", it is especially preferred to dilute it prior to addition to the column. Dilution is performed using the low ionic strength solution referred to supra. The sample may be diluted almost ad libitum, practical considerations such as column capacity determining what degree of dilution is appropriate. Any dilution with reason is feasible but it is preferable to dilute the sample anywhere from about a 1:1 to about a 1:3 ratio (sample: diluent).

After the sample is added to the column and remains for an amount of time sufficient to permit exchange of nucleic acid and bound ions, preferably about 10 minutes, but this can vary, impurities are washed from the column or matrix. In the following description of the wash step, removal of the wash solution via centrifugation, gravity or other types of removal may be used.

A wash solution is added to the column following application of the sample. Application of the wash solution is performed without disturbance of the matrix bed. This solution is a weak ionic salt solution. "Weak", as used herein refers to a concentration of from about 0.05 M to about 0.5 M. "Salt" as used refers to an ionic salt, preferably NaCl. Other salts, for example LiCl, $K_3PO_4$, NaF, or KI, are also encompassed by the invention. The aim is to provide an anion which competes with the counter ion associated with the matrix.

In terms of concentration, the preferred concentration of the wash solution is about 0.3 M.

Following the removal of the wash solution, either an elution buffer is applied or a priming step takes place. The priming step involves application of an amount of a strong salt solution to the column without disturbing the matrix. "Strong" as used herein refers to a concentration which is greater than the concentration of the weak ionic salt solution, and is preferably from about 0.75 M to about 2.25 M. The various salts which may be used are the same as those useful in the wash solutron. The preferred concentration of the priming solution is about 1.75 M. The volume of priming solution used is critical, and may range from about ⅓ to about ⅔ of the volume of the matrix bed volume. The volume of the matrix column bed is an easily determined value, and methods for determining it need not be elaborated upon herein.

This priming step, surprisingly, does not cause the nucleic acid to elute from the column. Instead, it permits elution thereafter of column bound nucleic acids in a smaller amount of elution buffer.

An elution buffer is added to the column, matrix or support after the wash step or after the priming step, if the latter is used. The elution buffer is a strong ionic salt solution, as described above. Again, the preferred strength is 1.75 M, and the preferred salt is NaCl. The elution buffer is applied to the matrix without disturbing it. If a priming step is used, the volume of elution buffer required to remove all of the DNA is less than that required without this step. A minimum amount of elution buffer equal to about 4/3 of the column bed volume is all that is required when a priming step is used. For example, if the column bed has a volume of 1.5 ml, than .5 ml of priming solution and 2.0 ml of elution buffer are sufficient. Upon removal via elution, e.g., the elution buffer contains the nucleic acids. The nucleic acid may then be precipitated, or otherwise treated, depending upon the requirements of the particular investigation.

The foregoing is a generalized protocol for the operation of the invention. The following examples are provided to teach the preferred embodiments of the generalized protocol given supra. They are not intended, and should not be read, as limitations on the scope of the invention.

EXAMPLE 1: SAMPLE PREPARATION

The following examples deal with purification of DNA from different cell and tissue samples. The procedure for sample preparation and lysis will be seen to vary with different sample sources. Once the cell lysate is obtained, however, it is treated the same, regardless of source, throughout the remaining stages of DNA purification.

A. Bacterial Cells

Up to $10^{10}$ cells may be prepared in this procedure when a matrix bed volume equal to 1.5 ml is used. Cells are spun at 12,000 × g for 5 minutes at 4° C. This yields a pellet and supernatant. The supernatant is discarded, and the pellet is washed with cold, sterile $H^2O$.

The pellet i in 2 ml of lysis solution (0.5 M guanidine HCl, 10 mM Tris (tris(hydroxymethyl)aminomethane), 1 mM EDTA, 10% betaine and 2% Triton-X) (octylphenoxypolyethoxyethanol), together with 60 ul RNase A (10 mg/ml) and 160 ul lysozyme (50 mg/ml). This is mixed via inversion and is incubated at 37° C. for 30 minutes.

The lysis reagent used herein is new. It is adaptable for use with both prokaryotic and eukaryotic samples, which is atypical. The lysis reagent is a composition comprising from about 1 to about 15 mM tris $^R$, from about .1 to about 2 mM EDTA, from about 1% to about 20% (w/v) an amphoteric surfactant, such as betaine, from about .1 to about 5% (v/v) of a neutral surfactant, such as Triton-X, and from about 0.5 to about 5 M guanidine HCl. A particularly preferred embodiment comprises about 10 mM Tris, about 1 mM EDTA, about 10% (w/v) betaine, about 2% Triton-X, and about 0.5 M guanidine HCl. The lysis reagent may be in the form of a "one pot" composition or in the form of a kit presenting separate containers of each of the recited elements, plus a means for holding these such as a box. The skilled artisan will note the absence of an anionic solvent in the reagent. This is generally required in cell lysis reagents, as exemplified by, e.g., SDS.

A quantity of 100 ul proteinase K (20 mg/ml) is then added, and mixed by inversion, followed by incubation is at 55–60° C. for 30 minutes.

The sample is then diluted in a 3 fold volume of wash solution (10 mM Tris, 1 mM EDTA and 0.3 M NaCl).

The sample is now ready for application to the column.

B. Mammalian Cells

The same protocol is followed as for bacterial cells, except that the cells are washed with 1X PBS prior to lysing and lysozyme is not added to the sample. Up to $10^9$ cell may be used with a matrix bed volume equal to 1.5 ml.

C. Solid Tissue

A 100 mg solid tissue sample is transferred to liquid nitrogen to freeze it. The frozen product is then ground to fines in a precooled mortar. This powder is then dissolved in 2 ml of lysis solution, as described supra, together with 60 ul RNAse A (10 mg/ml). This is mixed by gentle inversion, and is incubated at 37° C for 30 minutes. This is then mixed by inversion with 100 ul proteinase K (20 mg/ml), and is incubated at 55–60° C. for 3 hours. The sample is then diluted 3-fold by direct addition of 4 ml wash solution, as described supra.

D. Buffy Coat Sample

Draw up to 30 ml whole blood in the presence of an anticoagulant. Prepare a buffy coat sample from the whole blood using a Ficoll$^R$ gradient using standard techniques well known in and recognized by the art. Remove clarified buffy coat cells to a conical screw tap tube.

Resuspend the buffy coats in 2 ml lysis buffer, supra and add 60 ul RNase A (10 mg/ml). Mix by gentle inversion and incubate at 37° C for 30 minutes. Add 100 ul proteinase K (20 mg/ml). Mix by inversion and incubate at 55–60° C for 30 minutes. Dilute 3-fold by direct addition of 4 ml wash solution.

E. Mouse Tail

Place a 1.5 cm piece of fresh mouse tail in a precooled Eppendorf tube and set on ice. Singe off hair and dip tail in 95% ethanol. Wipe tail and mince well. Resuspend the sample in 2 ml of lysis buffer, as above, add 100 ul Proteinase K (20 mg/ml) and incubate at 55–60° C. overnight with constant shaking. After this incubation, the mixture should appear as a brownish sludge. Add 60 ul RNase A (10 mg/ml). Mix by inversion and incubate at 55–60° C. for 30 minutes. Dilute 3-fold by direct addition of 4 ml wash solution. Briefly spin sample to sediment large debris. Carefully pipette supernatant and apply to column.

EXAMPLE 2: COLUMN EQUILIBRATION

During the lysis procedure, the purification column is equilibrated. The column has applied thereto 6 ml of wash solution, as described supra, to the matrix surface. The wash solution is eluted by gravity, and is discarded. Tightly cap the bottom of the column prior to addition of sample.

EXAMPLE 3: PURIFICATION PROCEDURE

Using a 10 ml sterile pipette, the 6 ml sample, as prepared, e.g., in Example, supra, is applied to the column bed which has been equilibrated as in Example 2. The matrix surface is progressively disturbed, creating a uniformly mixed slurry.

In the best method of forming the lysate-matrix slurry known at the present time, the dispensing tip of a pipette containing the lysate is held just out of contact with the surface of the matrix. The lysate is then released to that it flows from the tipe in a slow stream which disturbs the surface of the matrix so that the particles of the matrix mix with the lysate to form a cloudy dispersion. The tip of the pipette is progressively lowered into the matrix while the stream is maintained so that a cloudy dispersion of matrix particles in the lysate is steadily produced from the top to the bottom of the column, resulting in a substantially uniformly mixed lysate-matrix slurry.

Although this is the preferred method, other less desirable methods of mixing can be used and are within the scope of the invention. For example, mixing can be by inversion, although this method can result in sticking of matrix particles throughout the inside of the column. It also undesirably increases shearing forces on the DNA so that the DNA risks fragmentation. Stirring can also be used, but it is less desirable because it threatens the integrity of the matrix material. This column bed is then allowed to settle for 10 minutes.

A bottom cap is removed and the column drains via gravity. If necessary, a 10 ml syringe may be used to apply pressure, but the flow rate should not exceed 0.5 ml/min.

The column matrix is then washed by adding about 3 ml of wash solution as described supra. This wash solution is eluted by gravity. Alternatively, the column is centrifuged at a low speed in a swinging bucket rotor for 1 minute at $41 \times g$, to elute the wash solution.

The wash solution is then collected and discarded.

Following this, 0.5 ml of priming solution, as described, is applied to the matrix bed and is eluted by gravity or by centrifugation.

The priming solution is then collected and discarded.

The column is then carefully placed in a new collection tube, where 2 ml of elution solution are applied. Again, either gravity or centrifugation can be used. The eluate contains the purified DNA, which can be further treated as indicated supra.

EXAMPLE 4

The protocol described in Examples 1-3 was followed in extracting nucleic acids from procaryote cells.

A sample E. coli strain MM294 ($10^{10}$ cells), were centrifuged at $12,000 \times g$ for 5 minutes at 4° C. yielding a pellet and supernatant. The supernatant was discarded and the pellet was washed with cold, sterile $H_2O$.

The pellet was resuspended in 2 ml of lysis solution described in Example 1, with 60 ul RNase A (10 mg/ml) and 160 ul lysozyme (50 mg/ml). The resulting combination was mixed, via inversion, and incubated at 37° C. for 30 minutes. Following this, 100 ul proteinase K (20 mg/ml) was added.

Following incubation, the sample was diluted 3-fold with washing solution, as described in Example 1 (10 mM Tris, 0.1 M EDTA and 0.3 M NaCl).

During sample lysis, the purification column had been equilibrated. In this example, a DEAE sepharose "Fast Flow" (Pharmacia; exclusion limit for globular protein: $4 \times 10^6$ daltons; dry bead diameter 45-165 um; ionic capacity 100-160 mmol/g; pH stability 2-14) column, was used, in a cartridge equipped with an entry and an exit port. Column equilibration was performed under the conditions described in Example 2.

Purification then took place following the protocol described in Example 3. The 6 ml lysed sample was applied to the DEAE Sepharose bed, progressively disturbing the matrix creating a uniformly mixed slurry. This step is important, and differs from standard and known protocols which require the user not to disturb the matrix surface.

The matrix settled for 10 minutes. The exit port was then opened, which results in drainage by gravity. Again, the provisos of Example 3 apply in terms of the application of pressure to secure steady flow rate.

The matrix was then washed via application of 3 ml wash solution (10 mM Tris, 0.1 M EDTA and 0.3 M NaCl), followed by centrifugation at low speed in a swinging bucket rotor for 1 minute at 41 x g to elute the wash solution. Alternatively, the wash solution may be removed by gravity.

Next approximately 0.5 ml priming solution (1.75 M NaCl) was applied carefully to the column without disturbing the matrix bed. The same centrifugation step used to elute the wash solution was used to elute the priming solution. Again, gravity may also be employed.

The priming step facilitates elution of the nucleic acids. Surprisingly, the priming step does not itself result in the loss of nucleic acids from the column, but it makes it possible to elute the nucleic acids using far less elution solution than previously believed possible. As a result, a more concentrated sample of nucleic acid results in the elution step, which is now described.

A 2 ml sample of elution reagent (10 mM Tris, 1 mM EDTA and 1.75 M NaCl) was added to the column, followed by centrifugation as described supra. Use of such a small volume of elution buffer is unique and is made possible through the priming step. The elution buffer was removed together with the purified DNA using centrifugation as described supra. Alternatively, gravity can be used.

The DNA was then analyzed via the use of various restriction endonucleases well known to the art. The digested DNA was electrophoresed on agarose and compared to sample of lambda phage/Hind III DNA molecular weight markers. These results are depicted in FIG. 1.

EXAMPLE 5

Eukaryotic nucleic acids were purified from a sample of rat hepatoma 3924A, following the protocol used in Example 4, except RNase was not used. The resulting purified nucleic acids thus contain RNA and DNA, as can be seen in FIG. 2.

In both Examples 4 and 5, the column purified DNA was digested by various restriction endonucleases requiring different salt concentrations. The digestion patterns displayed discrete bands as shown in FIGS. 1 and 2. The control DNA was intact high molecular weight DNA. The molecular weight of the control undigested column purified DNA as determined by pulsed field gel electrophoresis ranged between 50 and 200 kb. The 260/280 ratio of this column purified DNA ranged between 1.8 and 2.0.

The foregoing examples illustrate the use of the invention and its applicability to purification of total nucleic acids, as well as DNA. The skilled artisan will recognize that the substitution of DNase for RNase permits separation of either RNA or DNA when desired.

The examples show the applicability of the invention to both eukaryotic and prokaryotic samples. Among the types of samples which can be used are blood, serum, stool, urine, and other biological fluids. Various cell types, including bacteria, buffy coats (white blood cells), tumor cells, hybridomas, etc., may be treated to purify nucleic acid therefrom. With routine adaptation of protocols, one may also purify crude nucleic acid samples to obtain pure "subsamples" of desired DNA. Techniques such as polymerase chain reactions, RFLP analysis, sequencing, cloning, obtaining DNA for preparation of nucleic acid probes, and so forth are adaptable to the methodology described herein. Additional applications include pulsed field gel electrophoresis, and detection methodologies such as Southern and Northern Blotting.

The choice of anion exchange material used for the matrix may vary, the one critical factor being that it must be a material which facilitates exchange of a negative ion, such as chloride, with a negatively charged nucleic acid molecule. Generally the so-called "weak" exchangers are preferred. These "weak" anionic exchangers are ionized over a limited pH range (generally from about 6 to about 9). Where practicable, a so-called "strong" anion exchanger may also be used. There are many examples of both known to the art, and these need not be described here.

As well as the method described supra, the invention includes a reagent kit which is useful in separating nucleic acids from a sample. The kit contains at least a separate sample of each of the anionic exchange material, the weak salt solution which serves as the washing buffer, and the strong salt solution which serves as the elution buffer, and, optionally, as the priming solution as well. optionally the kit may contain a reagent system useful in releasing nucleic acids from a cell sample, e.g., these reagents systems include various materials such as lysozyme, RNase, proteinase K and so forth. A cell lysis reagent may be included in such systems. When it is, the novel reagent described herein maybe used.

It will be understood that the specification and examples are illustrative but not limitative of the present invention and that other embodiments within the spirit and scope of the invention will suggest themselves to those skilled in the art.

We claim:

1. Method for obtaining a pure sample of nucleic acid comprising:
    (a) applying a sample containing nucleic acid to an anionic exchange material in a column,
    (b) mixing said sample with said anionic exchanger material to form a uniform slurry therebetween,
    (c) applying a weak ionic salt solution which contains no organic solvents to said anionic exchange material, wherein said weak ionic salt solution has a concentration of from about 0.05M to about 0.5M,
    (d) removing said weak ionic salt solution from said anionic exchange material, and
    (e) eluting nucleic acid from said anionic exchange material by applying a strong ionic salt solution which contains no organic solvents thereto, said strong ionic salt solution having a concentration of from about 0.75M to about 2.25M.

2. Method of claim 1, further comprising equilibrating said anionic exchange material with said weak ionic salt solution prior to applying said sample thereto.

3. Method of claim 1, wherein said weak ionic salt solution has a concentration of about 0.3 M.

4. Method of claim 1-, wherein said strong ionic salt solution has a concentration of about 1.75 M.

5. Method of claim 1, further comprising diluting said sample with an amount of said weak ionic salt solution equal to up to about 3 times the volume of said sample.

6. Method of claim 1, wherein said anionic exchange material is DEAE sepharose.

7. Method of claim 1, wherein said ionic salt is NaCl.

8. Method of claim 1, wherein said weak solution and said strong solution of ionic salt are removed by gravity.

9. Method of claim 1, wherein said weak solution and said strong solution of ionic salt are removed by centrifugation.

10. Method of claim 1, further comprising applying a priming solution to said anionic exchange material after removal of said weak ionic salt solution and before eluting said nucleic acids therefrom, said priming solution comprising a strong ionic salt solution having a concentration of from about 0.75 M to about 2.25 M and being applied in an amount ranging from about ⅓ to about ⅔ of the volume of said anionic exchange material, and removing said priming solution.

11. Method of claim 1, wherein said eluting comprises applying said strong ionic salt solution in an amount which is at least 4/3 the volume of said anionic exchange material.

12. Method of claim 10, wherein said priming solution has a concentration of about 1.75 M.

13. Method of claim 10, wherein said priming solution is a strong NaCl solution.

14. Method of claim 1, wherein said nucleic acid is DNA.

15. Kit useful in separating non-plasmid nucleic acid from a sample, comprising a separate portion of each of:
    (i) an anionic exchange material,
    (ii) a weak ionic salt solution which contains no organic solvents at a concentration of from about 0.05M to about 05M,
    (iii) a strong ionic salt solution which contains no organic solvents at a concentration of from about 0.7M to about 2.25M, and
    (iv) a container means for holding (i), (ii) and (iii).

16. Kit of claim 15, further comprising a reagent system for lysing a sample containing cells.

17. Kit of claim 16, further comprising lysozyme and proteinase K.

18. Kit of claim 15, wherein said anionic exchange medium is DEAE sepharose.

19. Kit of claim 15, wherein said weak ionic salt solution is at a concentration of about 0.3 M.

20. Kit of claim 15, wherein said strong ionic salt solution is at a concentration of about 1.75 M.

21. Kit of claim 15, wherein said ionic salt for both said weak and said strong solution is NaCl.

22. Kit of claim 18, wherein said lysing solution comprises from about 1 to about 15 mM Tris, from about .1 to about 2 mM EDTA, from about 1 to about 20% w/v of an amphoteric surfactant, from about .1 to about 5% v/v of a neutral surfactant, and from about 0.5 to about 5 M guanidine HCl.

23. Kit of claim 22, wherein said amphoteric surfactant is betaine, and said neutral surfactant is octylphenoxy polyethoxyethanol.

24. Kit of claim 23, wherein said lysing solution comprises about 10 mM Tris, about 1 mM EDTA, about 10% w/v betaine, about 2% v/v octylphenoxy polyethoxyethanol, and about 0.5 M guanidine HCl.

25. Composition useful in lysing a sample containing cells comprising from about 1 to about 15 mM tris (hydroxy-methyl) aminomethan from about .1 to about 2 mM EDTA, from about 1 to about 20% w/v of an amphoteric surfactant, from about .1 to about 5% v/v of a neutral surfactant, and from about 0.5 to about 5 M guanidine HCl.

26. Composition of claim 25, wherein said amphoteric surfactant is betaine, and said neutral surfactant is octylphenoxy polyethoxyethanol.

27. Composition of claim 26, wherein said lysing solution comprises about 10 mM tris (hydroxy-methyl) aminomethane, about 1 mM EDTA, about 10% w/v betaine, about 2% v/v octylphenoxy polyethoxyethanol, and about 0.5 M guanidine HCl.

* * * * *

UNITED STATES PATENT AND TRADEMARK OFFICE
CERTIFICATE OF CORRECTION

PATENT NO. : 4,997,932

DATED : March 5, 1991

INVENTOR(S) : Melissa Reardon et al

It is certified that error appears in the above-identified patent and that said Letters Patent is hereby corrected as shown below:

Column 5, line 62, change "i" to --is resuspended--.

Column 10, line 52, change "05M" to --0.5M--.

line 55, change "0.7M" to --0.75M--.

Column 11, claim 22, line 1, change "18" to --16--.

Signed and Sealed this

First Day of December, 1992

Attest:

DOUGLAS B. COMER

Attesting Officer      Acting Commissioner of Patents and Trademarks